United States Patent [19]
Wise

[11] Patent Number: 5,855,539
[45] Date of Patent: Jan. 5, 1999

[54] KINESIOLOGY TESTING APPARATUS

[76] Inventor: Raymond Wise, 300, 52112 Range Rd. 222, Sherwood Park, Alberta, Canada, T8C 1H6

[21] Appl. No.: 645,588

[22] Filed: May 14, 1996

[51] Int. Cl.⁶ ..................................................... A63B 21/00
[52] U.S. Cl. ............................. 482/91; 482/125; 482/907
[58] Field of Search .................................. 482/146, 125, 482/79, 80, 121, 122, 129, 130; 128/774; 74/380, 379; 73/379.03, 379.01, 379.08, 862.02; 600/587, 595, 592

[56] References Cited

U.S. PATENT DOCUMENTS

| | | | |
|---|---|---|---|
| 1,372,026 | 7/1921 | Hutter | 482/123 |
| 3,792,860 | 2/1974 | Selnes | 482/80 |
| 5,178,596 | 1/1993 | McIntire | 482/125 |

*Primary Examiner*—Jerome W. Donnelly
*Attorney, Agent, or Firm*—Anthony R. Lambert

[57] ABSTRACT

A kinesiology testing apparatus which includes a base. A foot treadle is provided having a first end and a second end. The first end is pivotally attached to the base. A line is provided having a first end and a second end. The second end is secured adjacent to the second end of the foot treadle. Means is provided for securing the first end of the line to a person's arm. When a person has his arm extended out parallel to a floor, a downward force exerted by a foot of the person upon the foot treadle is transmits, via the line, a downward force upon the person's arm.

1 Claim, 2 Drawing Sheets

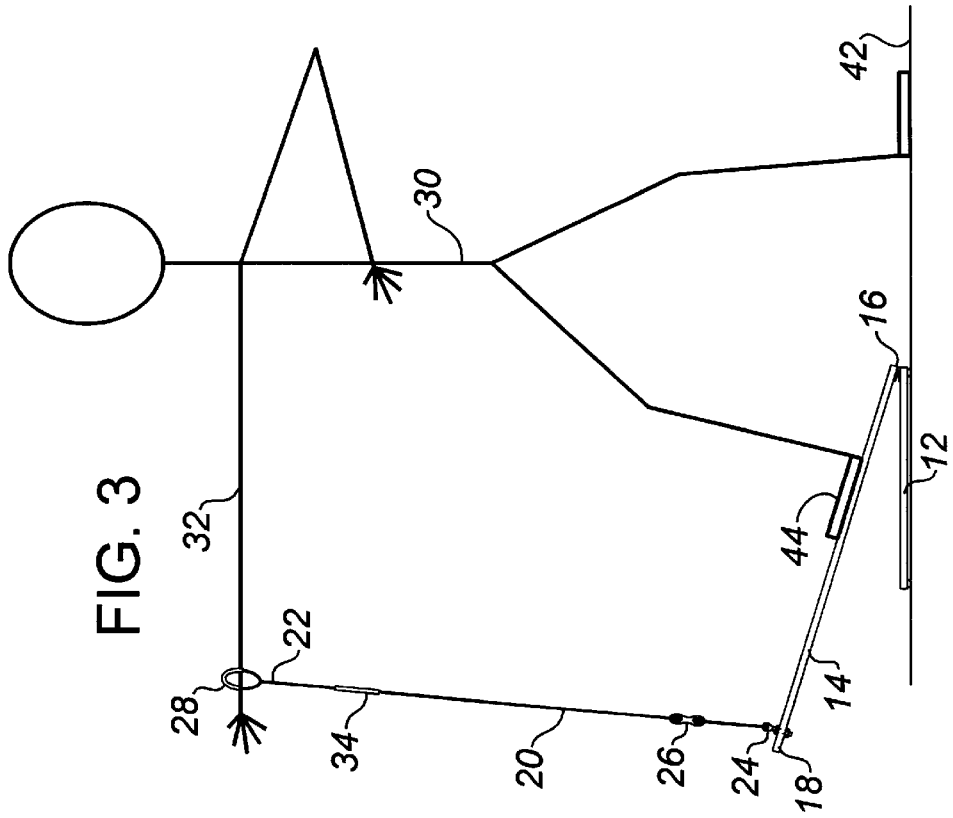
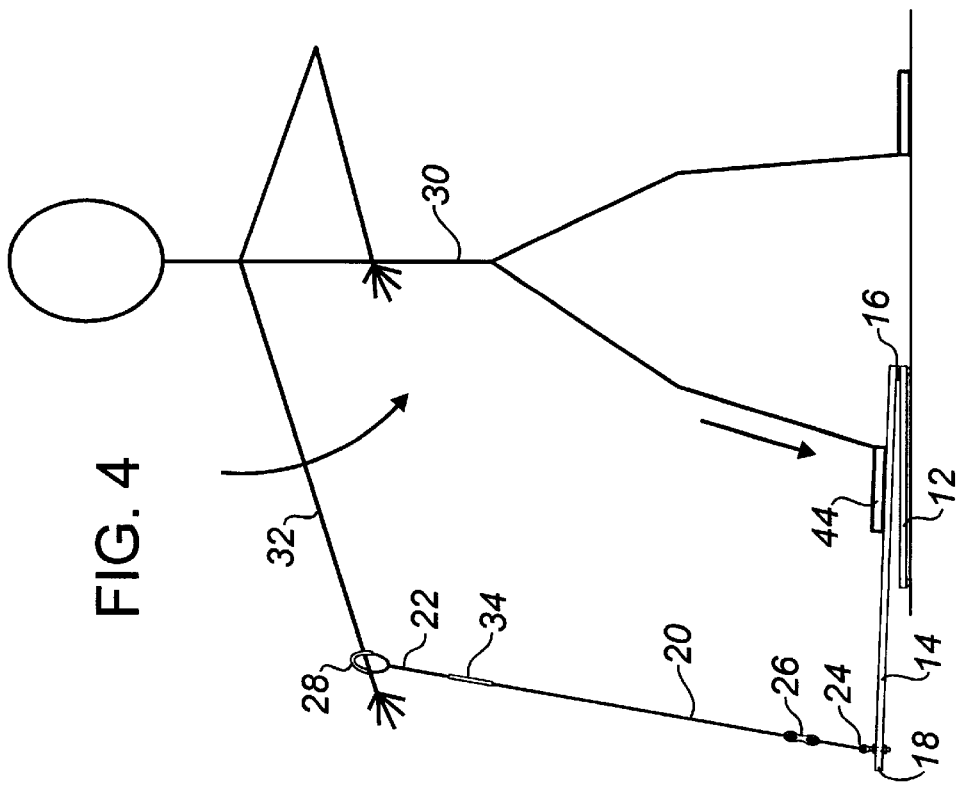

KINESIOLOGY TESTING APPARATUS

FIELD OF THE INVENTION

The present invention relates to a testing apparatus for use in that branch of holistic medicine known as applied kinesiology.

BACKGROUND OF THE INVENTION

"Applied kinesiology" is a term used to describe a branch of holistic medicine that studies the relationship between muscle movement and the health of the human body. Once the principles of applied kinesiology are understood, it can be used as a noninvasive diagnostic tool. By way of example only, one use of applied kinesiology is in testing for allergies and sensitivities to food.

Some books which describe the underlying principles of applies Kinesiology include:

"Applied Kinesiology"—Tom and Carole Valentine, (1985) Healing Arts Press, One Park Street, Rochester, Vt., 05767;

"Your Body Doesn't Lie"—John Diamond, (1980) Warner Books, Inc., 1271 Avenue of the Americas, New York, N.Y., 10020;

"Thorsons Introductory Guide to Kinesiology—Touch for Health" Maggie La Tourelle and Anthea Courtenay, (1992) Thorsons (HarperCollins Publishers) 77–85 Fulham Palace Road, Hammersmith, London, W6 8JB.

In applied kinesiology, muscles are tested to determine the quality of the response. This testing can involve complex electronic equipment, but more commonly involves one or more simple muscle tests. A test recommended by Dr. John Diamond in "Your Body Doesn't Lie" uses the muscles in the arms as "indicator muscles". Roughly paraphrased, the method advocated by Dr. Diamond involves the following steps. Firstly, have the subject extend one arm out parallel to the floor. Secondly, push down on the arm quickly and firmly. The purpose is not to push with such force or over such a time duration that the muscle becomes fatigued; rather the purpose is to determine whether the muscle can lock the shoulder joint against the push. Thirdly, perform the test again as the subject chews a food product. It is the contention of Dr. Diamond that if there is a allergy or sensitivity to the food being ingested, there will be a marked difference in the response when the test is repeated. On page 9 of his book Dr. Diamond describes this difference in response as follows:

"The results will be dramatic. In nearly every case the subject will be unable to resist the pressure. His arm will go down easily."

At the present time, people who follow the teachings of Applied Kinesiology must consult a qualified individual, such as Dr. Diamond, in order to be tested. It is not possible for an individual to test himself or herself. This results in unavoidable time delays and necessarily entails some expense.

SUMMARY OF THE INVENTION

What is required is a kinesiology testing apparatus which permits testing to be self administered.

According to the present invention there is provided a kinesiology testing apparatus which includes a base. A foot treadle is provided having a first end and a second end. The first end is pivotally attached to the base. A line is provided having a first end and a second end. The second end is secured adjacent to the second end of the foot treadle. Means is provided for securing the first end of the line to a person's arm. When a person has his arm extended out parallel to a floor, a downward force exerted by a foot of the person upon the foot treadle is transmits, via the line, a downward force upon the person's arm.

With the kinesiology testing apparatus, as described above, a person can test oneself in a manner that is intended to resemble, as closely as possible, the manner of testing performed by a kinesiology professional.

Although beneficial results may be obtained through the use of the kinesiology testing apparatus, as described above, people come in a wide range of sizes. Even more beneficial results may, therefore, be obtained when means are provided for adjusting the length of the line. This enables more than one person in a household, for example a husband and a wife, to use the same apparatus with only a minor adjustment.

Although beneficial results may be obtained through the use of the kinesiology testing apparatus, as described above, in order for an unexperienced person to obtain valid results care must be taken to exert the same amount of pressure for each series of tests. Even more beneficial results may, therefore, be obtained when resistance measuring means is provided along the line, thereby providing an objective indication of the force exerted upon the line.

BRIEF DESCRIPTION OF THE DRAWINGS

These and other features of the invention will become more apparent from the following description in which reference is made to the appended drawings, wherein:

FIG. 3 is a side elevation view of the kinesiology testing apparatus illustrated in FIG. 1, positioned on a person in a first or initiating position.

FIG. 4 is a side elevation view of the kinesiology testing apparatus illustrated in FIG. 1, positioned on a person in a second or completing position.

DETAILED DESCRIPTION OF THE PREFERRED EMBODIMENT

Figure 1:
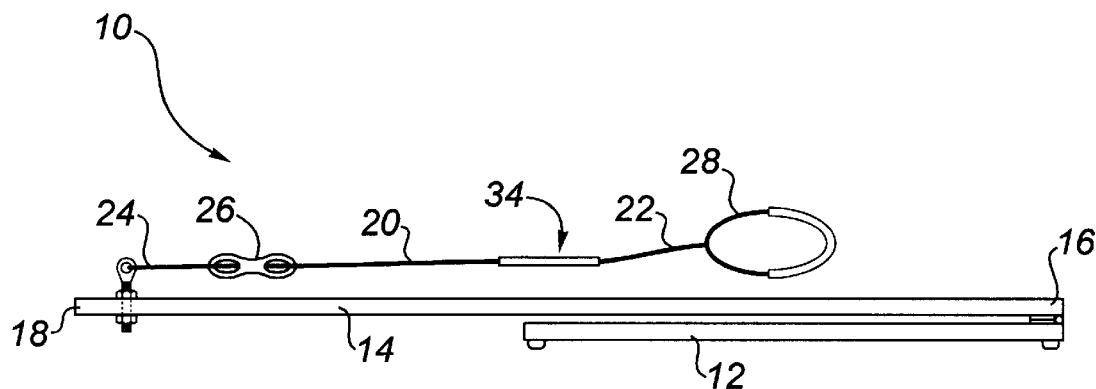
FIG. 1 is a side elevation view of a kinesiology testing apparatus constructed in accordance with the teachings of the present invention.

The preferred embodiment, a kinesiology testing apparatus generally identified by reference numeral 10, will now be described with reference to FIGS. 1 through 4.

Figure 2:
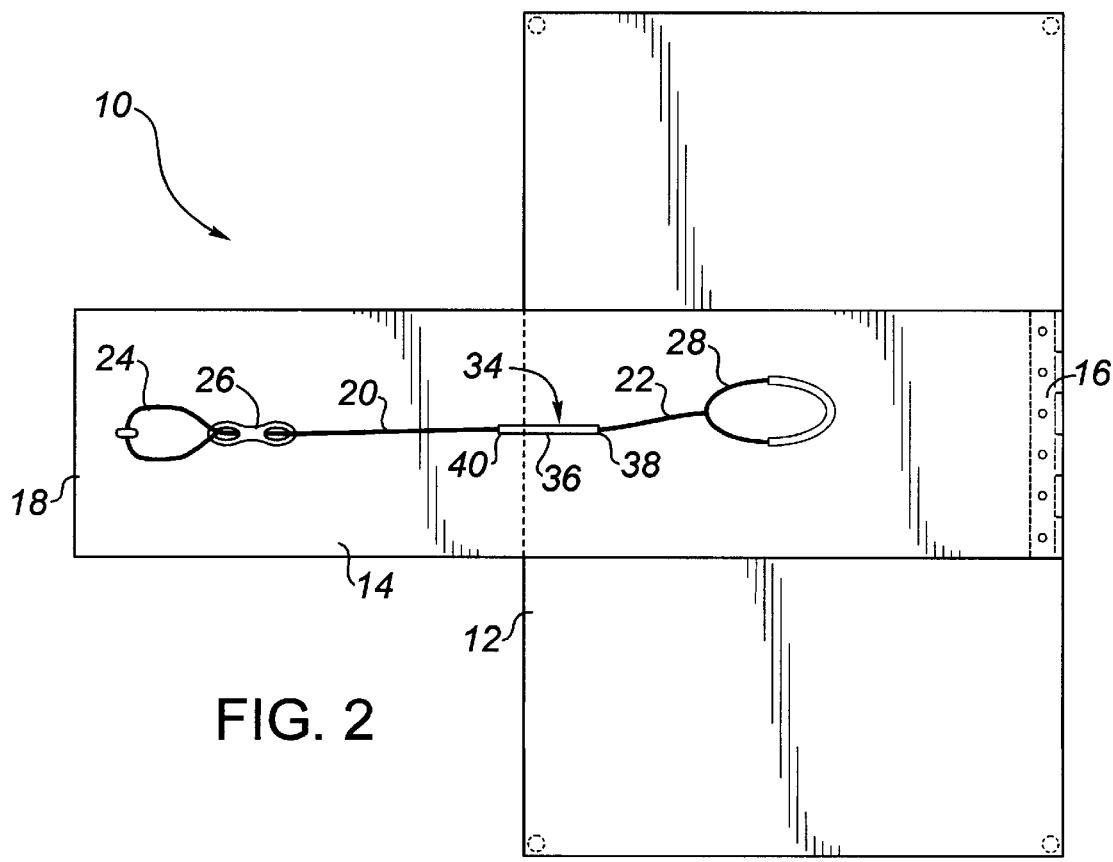
FIG. 2 is a top plan view of the kinesiology testing apparatus illustrated in FIG. 1.

Referring to FIGS. 1 and 2, kinesiology testing apparatus 10 includes a planar base 12. A foot treadle 14 is provided having a first end 16 and a second end 18. First end 16 is pivotally attached to base 12. A line 20 is provided having a first end 22 and a second end 24. Second end 24 is secured adjacent to second end 18 of foot treadle 14. A line adjusting device 26 in the general shape of a figure "8" is provided means for adjusting the length of line 20. A loop 28 is positioned at first end 22 of line 20. Referring to FIGS. 3 and 4, it is by means of loop 28 that first end 22 of line 20 is secured to a person's 30 arm 32. Referring to FIGS. 1 and 2, a resistance measuring scale 34 is spliced into line 20. Resistance measuring scale 34 includes a body 36 having a first end 38 and a second end 40. There are a variety of resistance measuring scales 34 commercially available, and the internal workings of the same will not be further described. One example of such a resistance measuring scale is a spring scale in which first end 38 and second end 40 move telescopically relative to one another when a force is exerted. A visual indicator scale (not shown) on resistance measuring scale 34 serves as means for indicating the force exerted upon body 36 when body 36 is placed in tension. This provides an objective indication of the force exerted upon line 20.

The use and operation of kinesiology testing apparatus 10 will now be described with reference to FIGS. 1 through 4. Referring to FIG. 3, person 30 places loop 28 over his arm 28 and extends his arm out parallel to a floor or ground surface 42. Referring to FIG. 4, a downward force is then exerted by a foot 44 of person 30 upon foot treadle 14. This force is transmitted, via line 20 and exerts a downward force upon person's 30 arm 32. The testing is carried out in the manner advocated by Dr. Diamond. A first test is taken using arm 32 as an indicator muscle. A second test is then taken as a food is being chewed to determine whether there is an objective difference in resistance. An objective difference in resistance is an indication of the bodies intolerance for the tested food.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A method for kinesiology testing, comprising the steps of:

firstly, providing a kinesiology testing apparatus, comprising:
 a base;
 a single foot treadle having a first end and a second end, the first end being pivotally attached to the base;
 a line having a first end and a second end, the second end being secured to the second end of the foot treadle; and
 means for securing the first end of the line to a person's arm, secondly, securing the first and of the line to an arm of a person;

thirdly, having the person extend the arm out horizontally; and fourthly, exerting a downward force upon the arm by stepping upon the foot treadle.

* * * * *